United States Patent [19]
Kiel

[11] Patent Number: 5,716,344
[45] Date of Patent: Feb. 10, 1998

[54] APPARATUS FOR SUPPORTING A DRAINAGE RESERVOIR AT A LOCATION ADJACENT TO A PATIENT'S BODY

[75] Inventor: Judy Kiel, Columbus, Ind.

[73] Assignee: Juji, Inc., Columbus, Ind.

[21] Appl. No.: 759,871

[22] Filed: Dec. 3, 1996

[51] Int. Cl.⁶ ..................................... A61M 25/00
[52] U.S. Cl. .......................... 604/174; 604/179; 604/180
[58] Field of Search ...................... 604/174, 179, 604/180; 128/DIG. 15, DIG. 26

[56] References Cited

U.S. PATENT DOCUMENTS

| | | |
|---|---|---|
| 2,699,782 | 4/1954 | Chester . |
| 3,730,187 | 5/1973 | Reynolds ................. 128/DIG. 26 X |
| 4,073,295 | 2/1978 | Laufbahn . |
| 4,122,851 | 10/1978 | Grossner . |
| 4,149,540 | 4/1979 | Hasslinger . |
| 4,422,455 | 12/1983 | Olsen ...................... 128/DIG. 15 X |
| 4,864,698 | 9/1989 | Brame . |
| 4,901,375 | 2/1990 | Dahlgren . |
| 5,087,251 | 2/1992 | Heyman et al. . |
| 5,237,988 | 8/1993 | McNeese ................. 128/DIG. 26 X |
| 5,341,802 | 8/1994 | Calebaugh .............. 128/DIG. 26 X |
| 5,429,623 | 7/1995 | Dessel . |
| 5,439,456 | 8/1995 | Fabricant . |
| 5,445,149 | 8/1995 | Rotolo et al. ........................ 128/644 |
| 5,513,633 | 5/1996 | Islava ...................... 128/DIG. 26 X |
| 5,529,062 | 6/1996 | Byrd ....................... 128/DIG. 26 X |

FOREIGN PATENT DOCUMENTS

82/04399  12/1982  WIPO ................................. 604/174

OTHER PUBLICATIONS

Product Brochure–Closed Wound Drainage System, Copyright 1995 Johnson & Johnson Medical Inc., Arlington, TX.

Primary Examiner—Sam Rimell
Attorney, Agent, or Firm—Maginot, Addison & Moore

[57] ABSTRACT

A drainage reservoir and belt assembly includes a drainage reservoir, and a belt for supporting the drainage reservoir. The belt includes an elongated elastic strap having a first end portion and a second end portion. The belt further includes a first loop-hook fastener segment secured to the first end portion of the elastic strap. In addition, the belt includes a first buckle secured to the second end portion of the elastic strap, wherein (1) the first buckle has a first buckle opening defined therein, (2) the elastic strap extends through the first buckle opening, and (3) the first buckle is positionable at any one of a plurality of positions along a length of the elastic strap. Moreover, the belt includes a second buckle having a second buckle opening defined therein, wherein (1) the elastic strap extends through the second buckle opening of the second buckle, and (2) the second buckle is positionable at any one of a plurality of positions along the length of the elastic strap. The belt also includes a second loop-hook fastener segment secured to the second buckle, wherein the first loop-hook fastener segment is adapted to engage with the second loop-hook fastener segment.

18 Claims, 3 Drawing Sheets ns: 5,716,344

APPARATUS FOR SUPPORTING A DRAINAGE RESERVOIR AT A LOCATION ADJACENT TO A PATIENT'S BODY

BACKGROUND OF THE INVENTION

The present invention relates generally to support devices, and more specifically to an apparatus for supporting a drainage reservoir at a location adjacent to a patient's body.

Numerous straps and belts have heretofore been designed to support various objects adjacent to an individual's body. For example, there are many instances in which an individual having medical needs is required to wear a portable device which can receive body fluids. One such instance is after a medical procedure such as cancer surgery.

For a period of time after a surgical procedure is performed on a patient, a drainage reservoir is required to be worn by a patient in order to drain away body fluids from the surgical site. In particular, one end of a drainage tube is positioned in the area of the surgical site while the other end is positioned in fluid communication with a drainage reservoir. Thus, excess fluids generated by the body at the surgical site as a result of the trauma of the surgical procedure is removed from the body.

Various devices and methods have heretofore been used to support the drainage reservoir at a location adjacent to the patient's body. For example, patients have used safety pins to fasten the drainage reservoir to their clothing. However, this approach causes the patient to be less independent since assistance may be required to manipulate the pin while holding the drainage reservoir in place during the pinning process. This approach also has the disadvantage that the sharp end of the pin may become inadvertently unhooked and may prick the patient thus causing pain to the patient. In addition, when the drainage reservoir is secured directly to the patient's clothing, it is possible that the clothing may be improperly removed from the patient's body before the drainage reservoir has been unsecured from the patient's clothing thereby causing the drainage tube to be undesirably pulled out of the patient's body thus resulting in pain to the patient.

The above-mentioned problems cause this approach to be undesirable. The undesirability of this approach becomes compounded when two or more drainage reservoirs are required to be worn by a patient.

Other approaches to support a drainage reservoir adjacent to a patient's body have included the use of belts. However, these belts were not designed to allow the belt to be quickly and conveniently adjusted to the size of the patient. Moreover, some of these belts have been made of a material such as leather which is inflexible, bulky, uncomfortable to a patient during use, and less able to withstand multiple washings in a washing machine.

Therefore, what is needed is an apparatus for supporting a drainage reservoir at a location adjacent to a patient's body which is easy and convenient to use. What is further needed is an apparatus for supporting a drainage reservoir at a location adjacent to a patient's body which as comfortable to wear. Additionally, what is needed is an apparatus for supporting a drainage reservoir at a location adjacent to a patient's body which eliminates the risk of injury and pain due to inadvertent release of a sharp end of a safety pin.

SUMMARY OF THE INVENTION

In accordance with a first embodiment of the present invention, there is provided an apparatus for supporting a drainage reservoir at a location adjacent to a patient's body, with the drainage reservoir having a support loop attached thereto. The apparatus includes an elongated elastic strap which is extendible through the support loop, wherein the elastic strap has a first end portion and a second end portion. The apparatus further includes a first loop-hook fastener segment secured to the first end portion of the elastic strap. In addition, the apparatus includes a first buckle secured to the second end portion of the elastic strap, wherein (1) the first buckle has a first buckle opening defined therein, (2) the elastic strap extends through the first buckle opening, and (3) the first buckle is positionable at any one of a plurality of positions along a length of the elastic strap. Moreover, the apparatus includes a second buckle having a second buckle opening defined therein, wherein (1) the elastic strap extends through the second buckle opening of the second buckle, and (2) the second buckle is positionable at any one of a plurality of positions along the length of the elastic strap. Additionally, the apparatus includes a second loop-hook fastener segment secured to the second buckle, wherein the first loop-hook fastener segment is adapted to engage with the second loop-hook fastener segment.

In accordance with another embodiment of the present invention there is provided a drainage reservoir and belt assembly. The assembly includes a drainage reservoir, and a belt for supporting the drainage reservoir. The belt includes an elongated elastic strap having a first end portion and a second end portion. The belt further includes a first loop-hook fastener segment secured to the first end portion of the elastic strap. In addition, the belt includes a first buckle secured to the second end portion of the elastic strap, wherein (1) the first buckle has a first buckle opening defined therein, (2) the elastic strap extends through the first buckle opening, and (3) the first buckle is positionable at any one of a plurality of positions along a length of the elastic strap. Moreover, the belt includes a second buckle having a second buckle opening defined therein, wherein (1) the elastic strap extends through the second buckle opening of the second buckle, and (2) the second buckle is positionable at any one of a plurality of positions along the length of the elastic strap. The belt also includes a second loop-hook fastener segment secured to the second buckle, wherein the first loop-hook fastener segment is adapted to engage with the second loop-hook fastener segment.

In accordance with a further embodiment of the present invention there is provided an apparatus for supporting a drainage reservoir at a location adjacent to a patient's body, with the drainage reservoir having a support member attached thereto. The apparatus includes an elongated elastic strap which is extendible around the support member so that the support member can be interposed between the elastic strap and the patient's body, wherein the elastic strap has a first end portion and a second end portion. The apparatus further includes a first fastener segment secured to the first end portion of the elastic strap. In addition, the apparatus includes a first buckle secured to the second end portion of the elastic strap, wherein (1) the first buckle has a first buckle opening and a second buckle opening defined therein, (2) the elastic strap extends through the first buckle opening and the second buckle opening, and (3) the first buckle is positionable at any one of a plurality of positions along a length of the elastic strap. The apparatus also includes a second buckle having a third buckle opening and a fourth buckle opening defined therein, wherein (1) the elastic strap extends through the third buckle opening and the fourth buckle opening of the second buckle, and (2) the second buckle is positionable at any one of a plurality of positions along the length of the elastic strap. Additionally, the apparatus includes a second fastener segment secured to the second buckle, wherein the first fastener segment is adapted to engage with the second fastener segment.

It is therefore an object of the present invention to provide a new and useful apparatus for supporting a drainage reservoir at a location adjacent to a patient's body.

It is another object of the present invention to provide an improved apparatus for supporting a drainage reservoir at a location adjacent to a patient's body.

It is a further object of the present invention to provide a new and useful drainage reservoir and belt assembly.

It is yet another object of the present invention to provide an improved drainage reservoir and belt assembly.

It is moreover an object of the present invention to provide an apparatus for supporting a drainage reservoir at a location adjacent to a patient's body which is more comfortable to a user.

It is yet another object of the present invention to provide an apparatus for supporting a drainage reservoir at a location adjacent to a patient's body which is easier to use.

It is further an object of the present invention to provide an apparatus for supporting a drainage reservoir at a location adjacent to a patient's body which is less likely to injure the patient during use thereof.

It is moreover an object of the present invention to provide an apparatus for supporting a drainage reservoir at a location adjacent to a patient's body which allows a patient to be more independent.

It is yet another object of the present invention to provide an apparatus for supporting a drainage reservoir at a location adjacent to a patient's body which does not have to be secured to the patient's clothing.

It is a further object of the present invention to provide an apparatus for supporting a drainage reservoir at a location adjacent to a patient's body which can be quickly and conveniently secured to and released from a patient's body.

The above and other objects, features, and advantages of the present invention will become apparent from the following description and the attached drawings.

DETAILED DESCRIPTION OF THE INVENTION

Figure 1:
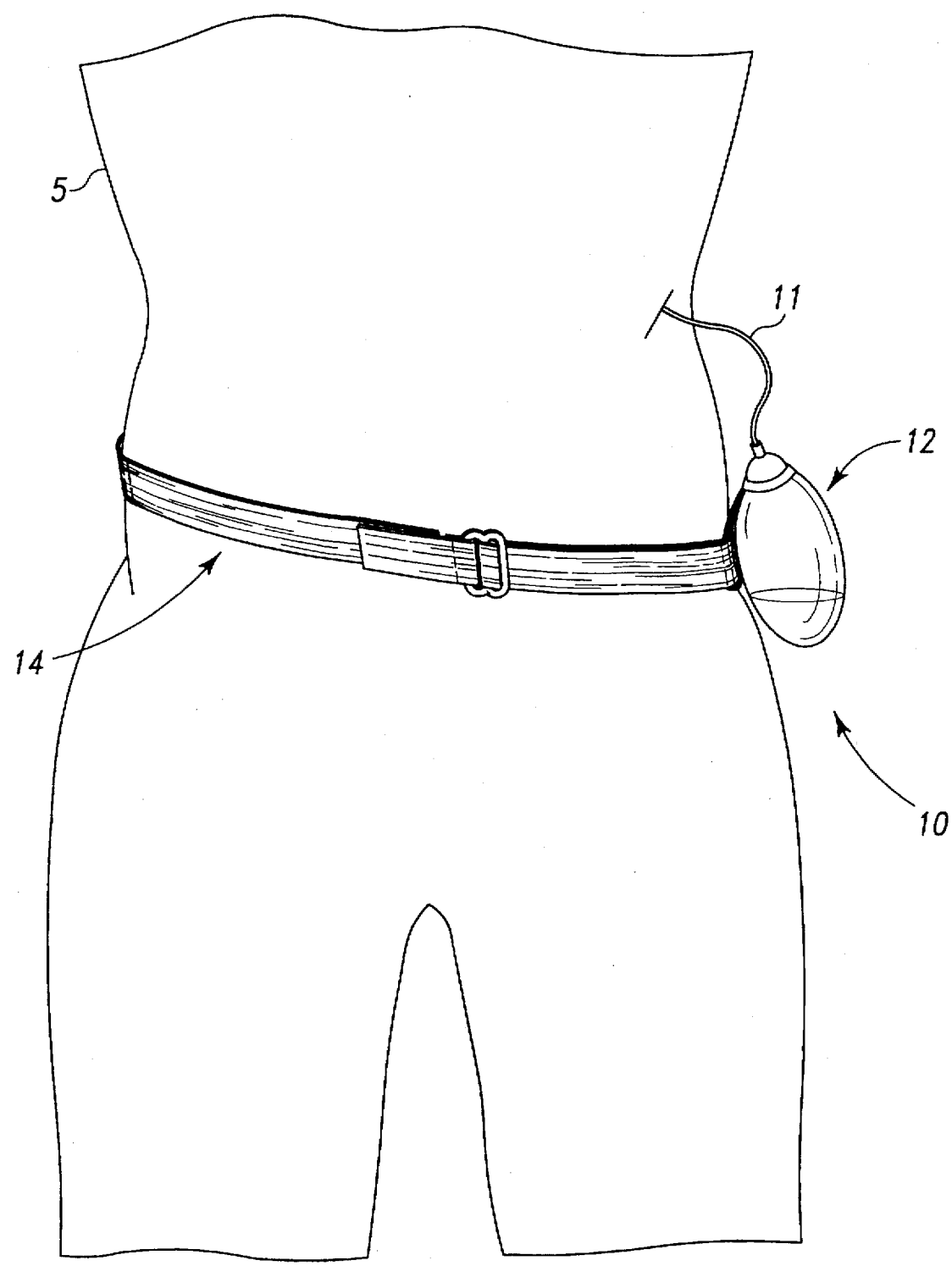
FIG. 1 is an elevational view of a drainage reservoir and belt assembly being worn by a patient which incorporates the features of the present invention therein.

While the invention is susceptible to various modifications and alternative forms, specific embodiments thereof have been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Referring now to FIG. 1, there is shown a patient's body 5 having a drainage reservoir and belt assembly 10 secured thereto. The assembly 10 includes a drainage reservoir 12 and a belt 14. The assembly 10 further includes a drainage tube 11 having a first end and a second end. The first end of the drainage tube 11 is positioned within the body 5 at a surgical site while the second end is positioned in fluid communication with the drainage reservoir 12. Thus, excess fluids generated by the body 5 at the surgical site as a result of trauma caused by a surgical procedure is removed from the body.

Figure 8:
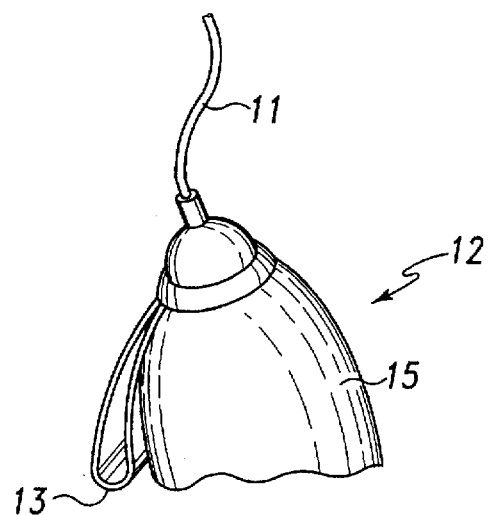
FIG. 8 is a fragmentary elevational view of the drainage reservoir of the drainage reservoir and belt assembly of FIG. 1.

The drainage reservoir 12 includes a container portion 15 (see FIG. 8) for receiving body fluids therein. The drainage reservoir 12 further includes a support loop 13 (see FIG. 8) connected to the container portion 15. When the assembly 10 is secured to body 5 as shown in FIG. 1, the belt 14 extends through the support loop 13 so as to support the drainage reservoir 12 at a location adjacent to the body 5. One drainage reservoir which may be used is a J-VAC Bulb Suction Reservoir available from Johnson & Johnson Medical of Arlington, Tex. 76004-3130.

Figure 2:
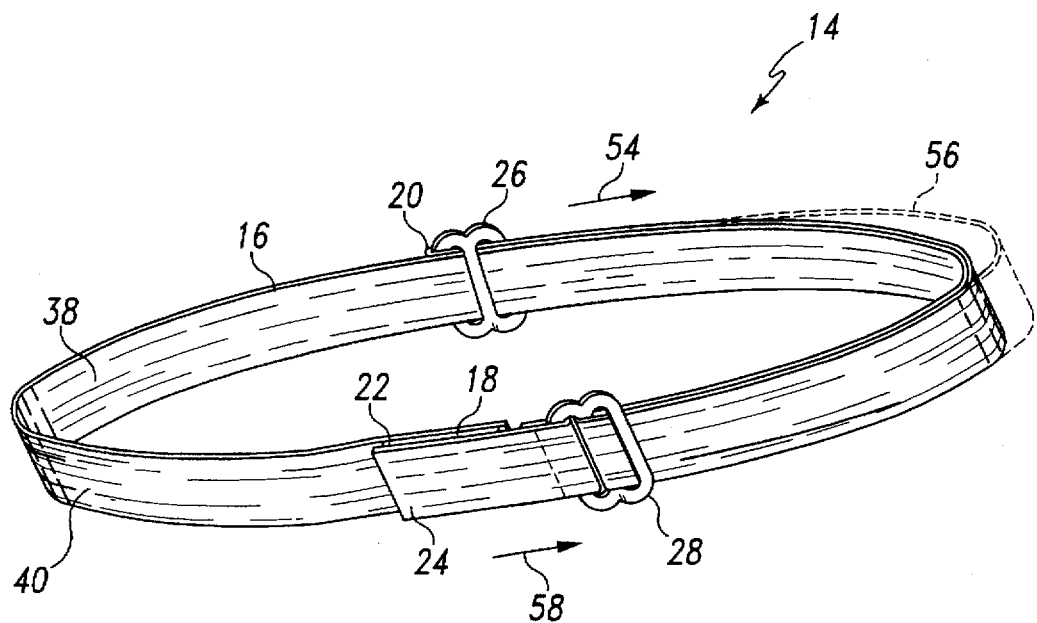
FIG. 2 is a perspective view of the belt of the drainage reservoir and belt assembly of FIG. 1.
Figure 3:
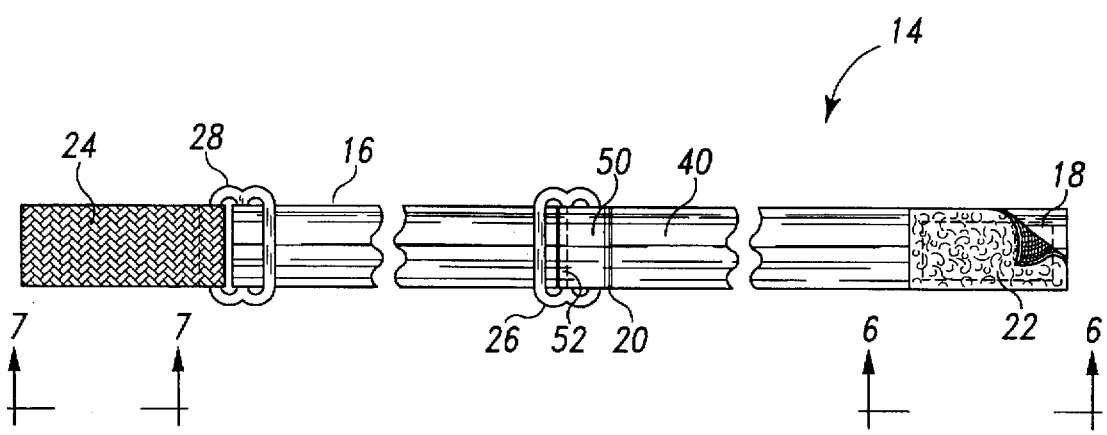
FIG. 3 is an elevational view of the belt of the drainage reservoir and belt assembly of FIG. 1.

Referring to FIGS. 2 and 3, the belt 14 includes an elongated elastic strap 16, a first loop-hook fastener segment 22, a second loop-hook fastener segment 24, a first buckle 26, and a second buckle 28.

The elongated elastic strap 16 is made of a waistband elastic material having a width of one (1) inch and a light color such as white. One waistband elastic material which may be used is a white knitted elastic material available from Lea & Sachs, Inc. of 1345 Golf Road, Des Plaines. Ill. 60017 as product number 1"#CM-217 white. During use of the assembly 10, the elastic strap is configured so as to define a patient contact side 38 and a visibly exposed side 40 as shown in FIG. 2.

Figure 6:
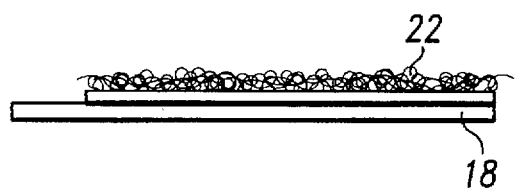
FIG. 6 is an elevational view taken along the lines 6—6 of FIG. 3 as viewed in the direction of the arrows.
Figure 7:
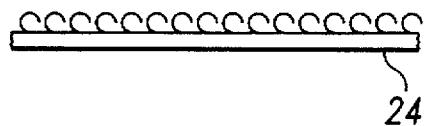
FIG. 7 is an elevational view taken along the lines 7—7 of FIG. 3 as viewed in the direction of the arrows.

The first loop-hook fastener segment 22 includes a plurality of upstanding loop-type engagement elements as shown in FIG. 6. The first loop-hook fastener segment 22 possesses a dark color such as black. The second loop-hook fastener segment 24 includes a plurality of upstanding hook-type engagement elements as shown in FIG. 7. The second loop-hook fastener segment 22 possesses a dark color such as black. One first loop-hook fastener segment and one second loop-hook fastener segment which may be used in the present invention are disclosed in U.S. Pat. No. 4,149,540 issued to Hasslinger, the disclosure of which is herein incorporated by reference.

Figure 4:
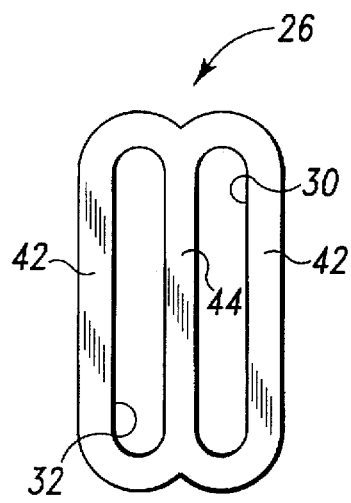
FIG. 4 is an elevational view of a first buckle of the belt of FIG. 2.
Figure 5:
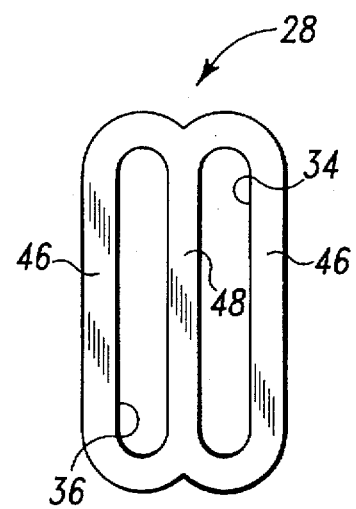
FIG. 5 is an elevational view of a second buckle of the belt of FIG. 2.

As shown in FIG. 4, the first buckle 26 includes a pair of buckle openings 30, 32 defined therein. The first buckle 26 further defines a pair of outer ribs 42 and a central rib 44. Similarly, as shown in FIG. 5, the second buckle 28 further includes a pair of buckle openings 34, 36 defined therein. The second buckle 28 further defines a pair of outer ribs 46 and a central rib 48.

The elongated elastic strap 16 has a first end portion 18 and a second end portion 20. The first loop-hook fastener 22 is secured to the first end portion 18 of the elastic strap 16 by sewing. The second end portion 20 of the elastic strap 16 is secured to the first buckle 26. In particular, the end portion 20 is manipulated relative to the first buckle 26 so as to extend through both buckle openings 30, 32 and form a loop 50 which extends around outer rib 42. Thereafter, the extreme end of the end portion 20 is sewn to another part of the end portion 20 so as to define a seam 52. It is important to note that the seam 52 of the sewn loop 50 is located on the visibly exposed side 40 of the elastic strap 16. This feature ensures that discomfort to the patient is avoided by not having seam 52 located directly against the body 5.

When it is desired to locate the drainage reservoir 12 at a location adjacent to the body 5 as shown in FIG. 1, the belt 14 is advanced through the support loop 13. Thereafter, the belt 14 is positioned around the body 5 at a desired location. The belt 14 is then stretched so that the first loop-hook fastener segment 22 is brought into contact with the second loop-hook fastener segment 24 so as to form an engagement therebetween. As a result of the above activity, a portion of support loop 13 is tightly interposed between the body 5 and elastic strap 16.

If the patient determines that the belt 14 is too tight around the body 5, the patient may first slide the first buckle 26 in a direction indicated by arrow 54 while the segment of the elastic strap 16 which defines the patient contact side 38 of the elastic strap near the first buckle 26 is maintained in a stationary position. This creates a surplus strap portion 56 as shown in phantom in FIG. 1. In order to eliminate this surplus strap portion 56, the elastic strap 16 is advanced through both buckle openings 34 and 36 of the second buckle 28 while maintaining the buckle 28 in a stationary position. The above activity loosens the belt 14 around the body 5.

For a fine adjustment of the tightness of the belt 14, the first loop-hook fastener 22 may be disengaged from the second loop-hook fastener 24. Thereafter, the second loop-hook fastener 24 may be advanced in the direction of arrow 58 while maintaining the first loop-hook fastener 22 in a stationary position. The second loop-hook fastener 24 may then be reengaged to the first loop-hook fastener 22.

Thus, it should be appreciated that the belt 14 provides for three manners of adjustment of the tightness of the belt around the body 5, while effectively supporting the drainage reservoir 12 at a location adjacent to the body 5 in a comfortable manner. The first manner is enabled by the inherent stretchability of the elastic strap 16, the second manner is enabled by the way in which the buckles 26, 28 cooperate with the elastic strap 16, and the third manner is enabled by the way in which the first loop-hook fastener 22 may be selectively located relative to the second loop-hook fastener 24 so as to form an engagement therebetween.

As discussed above, the first loop-hook fastener segment 22 and the second loop-hook fastener segment 24 each possess a dark color such as black, and the elastic strap 16 possesses a light color such as white. This feature enables a patient to easy discern which part of the belt 14 embodies the fastening segments 22, 24. This feature is especially helpful to elderly patients or other patients having impaired vision.

While the invention has been illustrated and described in detail in the drawings and foregoing description, such an illustration and description is to be considered as exemplary and not restrictive in character, it being understood that only the preferred embodiments have been shown and described and that all changes and modifications that come within the spirit of the invention are desired to be protected.

What is claimed is:

1. An apparatus for supporting a drainage reservoir at a location adjacent to a patient's body, with the drainage reservoir having a support loop attached thereto, comprising:

an elongated elastic strap which is extendible through said support loop, wherein said elastic strap has a first end portion and a second end portion;

a first loop-hook fastener segment secured to said first end portion of said elastic strap;

a first buckle secured to said second end portion of said elastic strap, wherein (1) said first buckle has a first buckle opening defined therein, (2) said elastic strap extends through said first buckle opening, and (3) said first buckle is positionable at any one of a plurality of positions along a length of said elastic strap;

a second buckle having a second buckle opening defined therein, wherein (1) said elastic strap extends through said second buckle opening of said second buckle, and (2) said second buckle is positionable at any one of a plurality of positions along the length of said elastic strap; and a second loop-hook fastener segment secured to said second buckle, wherein said first loop-hook fastener segment is adapted to engage with said second loop-hook fastener segment and wherein said elastic strap continuously overlaps for a distance which extends from said first buckle to said second buckle.

2. The apparatus of claim 1, wherein:

said first buckle has a third buckle opening defined therein, said second buckle has a fourth buckle opening defined therein, said elastic strap further extends through said third buckle opening of said first buckle, and said elastic strap further extends through said fourth buckle opening of said second buckle.

3. The apparatus of claim 1, wherein:

said first loop-hook fastener segment includes a plurality of upstanding loop-type engagement elements, and said second loop-hook fastener segment includes a plurality of upstanding hook-type engagement elements.

4. The apparatus of claim 1, wherein:

said first loop-hook fastener segment and said second loop-hook fastener each possesses a dark color, and said elastic strap possesses a light color.

5. The apparatus of claim 4, wherein:

said dark color is black, and said light color is white.

6. The apparatus of claim 1, wherein:

said elastic strap is configured during use of said apparatus to define a patient contact side and a visibly exposed side, said first buckle includes an outer rib, said second end portion of said elastic strap is sewn so as to form a sewn loop which extends around said outer rib, and a seam defined by said sewn loop is located on said visibly exposed side of said elastic strap.

7. An apparatus for supporting a drainage reservoir at a location adjacent to a patient's body, with the drainage reservoir having a support member attached thereto, comprising:

an elongated elastic strap which is extendible around said support member so that said support member can be interposed between said elastic strap and said patient's body, wherein said elastic strap has a first end portion and a second end portion;

a first fastener segment secured to said first end portion of said elastic strap;

a first buckle secured to said second end portion of said elastic strap, wherein (1) said first buckle has a first buckle opening and a second buckle opening defined therein, (2) said elastic strap extends through said first buckle opening and said second buckle opening, and (3) said first buckle is positionable at any one of a plurality of positions along a length of said elastic strap;

a second buckle having a third buckle opening and a fourth buckle opening defined therein, wherein (1) said elastic strap extends through said third buckle opening and said fourth buckle opening of said second buckle, and (2) said second buckle is positionable at any one of a plurality of positions along the length of said elastic strap; and a second fastener segment secured to said second buckle, wherein said first fastener segment is adapted to engage with said second fastener segment and wherein said elastic strap continuously overlaps for a distance which extends from said first buckle to said second buckle.

8. The apparatus of claim 7, wherein:

said first fastener segment is a first loop-hook fastener segment;

said second fastener segment is a second loop-hook fastener segment;

said first loop-hook fastener segment includes a plurality of upstanding loop-type engagement elements, and said second loop-hook fastener segment includes a plurality of upstanding hook-type engagement elements.

9. The apparatus of claim 7, wherein:

said first loop-hook fastener segment and said second loop-hook fastener each possesses a dark color, and said elastic strap possesses a light color.

10. The apparatus of claim 9, wherein:

said dark color is black, and said light color is white.

11. The apparatus of claim 7, wherein:

said elastic strap is configured during use of said apparatus to define a patient contact side and a visibly exposed side, said first buckle includes an outer rib, said second end portion of said elastic strap is sewn so as to form a sewn loop which extends around said outer rib, and a seam defined by said sewn loop is located on said visibly exposed side of said elastic strap.

12. A drainage reservoir and belt assembly, comprising:

a drainage reservoir; and a belt for supporting said drainage reservoir, wherein said belt includes the following:

an elongated elastic strap having a first end portion and a second end portion;

a first loop-hook fastener segment secured to said first end portion of said elastic strap;

a first buckle secured to said second end portion of said elastic strap, wherein (1) said first buckle has a first buckle opening defined therein, (2) said elastic strap extends through said first buckle opening, and (3) said first buckle is positionable at any one of a plurality of positions along a length of said elastic strap;

a second buckle having a second buckle opening defined therein, wherein (1) said elastic strap extends through said second buckle opening of said second buckle, and (2) said second buckle is positionable at any one of a plurality of positions along the length of said elastic strap; and a second loop-hook fastener segment secured to said second buckle, wherein said first loop-hook fastener segment is adapted to engage with said second loop-hook fastener segment and wherein said elastic strap continuously overlaps for a distance which extends from said first buckle to said second buckle.

13. The assembly of claim 12, wherein:

said first buckle has a third buckle opening defined therein, said second buckle has a fourth buckle opening defined therein, said elastic strap further extends through said third buckle opening of said first buckle, and said elastic strap further extends through said fourth buckle opening of said second buckle.

14. The assembly of claim 13, wherein:

said first loop-hook fastener segment includes a plurality of upstanding loop-type engagement elements, and said second loop-hook fastener segment includes a plurality of upstanding hook-type engagement elements.

15. The assembly of claim 12, wherein:

said first loop-hook fastener segment and said second loop-hook fastener each possesses a dark color, and said elastic strap possesses a light color.

16. The assembly of claim 15, wherein:

said dark color is black, and said light color is white.

17. The assembly of claim 12, wherein:

said elastic strap is configured during use of said apparatus to define a patient contact side and a visibly exposed side, said first buckle includes an outer rib, said second end portion of said elastic strap is sewn so as to form a sewn loop which extends around said outer rib, and a seam defined by said sewn loop is located on said visibly exposed side of said elastic strap.

18. The assembly of claim 12, wherein:

said drainage reservoir includes a support loop, and said elongated elastic strap extends through said support loop.

* * * * *